US007811763B2

(12) United States Patent
Poli et al.

(10) Patent No.: US 7,811,763 B2
(45) Date of Patent: Oct. 12, 2010

(54) OLIGONUCLEOTIDE PROBES FOR THE GENOMIC TYPIFYING OF ERYTHROCYTE SYSTEMS, METHODS AND RELATIVE DIAGNOSTIC KITS

(75) Inventors: Francesca Poli, Monza-Milan (IT); Francesca Drago, Milan (IT); Maria Antonietta Villa, Milan (IT); Alejandro Espadas De Arias, Buccinasco-Milan (IT); Loretta Crespiatico, Milan (IT)

(73) Assignee: Fondazione IRCCS Ca'Granda-Ospendale Maggiore Policlinico, Milan (IT)

( * ) Notice: Subject to any disclaimer, the term of this patent is extended or adjusted under 35 U.S.C. 154(b) by 80 days.

(21) Appl. No.: 11/795,827

(22) PCT Filed: Jan. 25, 2006

(86) PCT No.: PCT/IB2006/000224

§ 371 (c)(1),
(2), (4) Date: Sep. 10, 2007

(87) PCT Pub. No.: WO2006/079925

PCT Pub. Date: Aug. 3, 2006

(65) Prior Publication Data

US 2008/0299553 A1 Dec. 4, 2008

(30) Foreign Application Priority Data

Jan. 25, 2005 (IT) .......................... MI2005A0098

(51) Int. Cl.
*C12Q 1/68* (2006.01)
*C12P 19/34* (2006.01)
*C07H 21/04* (2006.01)

(52) U.S. Cl. ........................ 435/6; 435/91.1; 435/91.2; 536/24.3; 536/24.33

(58) Field of Classification Search ........................ None
See application file for complete search history.

(56) References Cited

U.S. PATENT DOCUMENTS 6,245,518 B1 * 6/2001 Baier ............................ 435/6

6,582,906 B1 * 6/2003 Cao et al. ..................... 435/6
2003/0143585 A1 * 7/2003 Stevens et al. ................. 435/6

FOREIGN PATENT DOCUMENTS

WO   WO 2005095650 A1 * 10/2005

OTHER PUBLICATIONS

Irshaid et al., "Novel alleles at the JK blood group locus explain the absence of the erythrocyte urea transporter in European families," British Journal of Haematology, 2002, vol. 116, pp. 445-453.*
Buck et al., "Design Strategies and Performance of Custom DNA Sequencing Primers," BioTechniques, 1999, vol. 27, pp. 528-536.*
Colinas Robert J, et al., Multiplexed genotyping of beta-golbin variants . . . , Clinical Chemistry, Jul. 2000, 996-998, vol. 46, No. 7., New York State Dept. of Health, NY.
Irshaid Nidal M., et al., Genomic typing of the Kidd blood . . . ,British Journal of Haematology, Sep. 1998, 1010-1014, vol. 102, No. 4, Blackwell Science Ltd., Lund, Sweeden.
Olives Bernandette, et al., The molecular basis of the Kidd blood group . . . , Human Molecular Genetics, 1997, 1017-1020, vol. 6, No. 7, Oxford University Press, Birmingham, UK.
Montalvo Lani, et al., Clinical investigation of posttransfusion Kidd blood group typing using a rapid normalized . . . , Transfusion, May 2004, 694-702, vol. 44, No. 5.
Ye F, et al., Fluorescent Microshere-based Readout Technology for Multiplexed Human . . . , Human Mutation, 2001, 305-316, vol. 17, No. 4, Wiley-Liss, New York, NY.
Fulton R. J., et al., Advanced multiplexed anaylsis with FlowMetrix system, Clinical Chemistry, Sep. 1997, 1749-1756, vol. 43, No. 9, Washington, DC.
Inagaki Sachiyo, et al., A new 39-plex anaylsis method for SNPs including 15 blood group loci, Forensic Science Intl., Aug. 2004, 45-57, vol. 144, No. 1, Elsevier Ireland Ltd.
Drago F, et al., Genotyping of the Kidd blood group with allele-specific . . . , Transfusion Medicine, Dec. 2005, 499-501, vol. 15, No. 6, Blackwell Publishing Ltd., England.
PCT Search Report, Dated Nov. 23, 2006.

* cited by examiner

*Primary Examiner*—Young J Kim
(74) *Attorney, Agent, or Firm*—Hedman & Costigan, P.C.; James V. Costigan

(57) ABSTRACT

The invention relates to oligonucleotide probes for the genomic typifying of erythrocyte systems, relative methods and diagnostic kits.

10 Claims, No Drawings

OLIGONUCLEOTIDE PROBES FOR THE GENOMIC TYPIFYING OF ERYTHROCYTE SYSTEMS, METHODS AND RELATIVE DIAGNOSTIC KITS

The present invention relates to specific oligonucleotide probes to be used in genomic typifying methods of erythrocyte systems and the relative diagnostic kits.

The typifying of erythrocyte antigenic systems is traditionally effected with agglutination methods in liquid phase or solid phase using commercial polyclonal or monoclonal antiserums. This technique is simple, can be applied in all laboratories and has an appropriate sensitivity and specificity in clinical use for most cases.

Agglutination tests, however, have various limitations mainly linked to the difficulty in evaluating the antigenic asset in some particularly risky conditions. These are mainly: a) the typifying of polytransfused immunized subjects; b) the identification of a fetus at the risk of hemolytic disease of newborn due to the presence of maternal antibodies; c) the determination of weak variants; d) the determination of zygosity for the RhD antigen; e) the determination of null phenotypes for erythrocyte antigens.

Furthermore, the use of agglutination techniques implies high costs in the case of mass screening in order to find negative donors for high incidence erythrocyte antigens. For some of these systems, the availability of commercial typifying reagents is extremely limited or non-existent.

One of the main advantages of DNA-based techniques is independence of reagents as the typifying serums are substituted by oligonucleotides which can be chemically synthesized at a low cost.

For this reason, various techniques based on DNA analysis have been developed for the typifying of erythrocyte systems on a molecular scale.

In particular, for the genotyping of erythrocyte antigenic systems, the most common techniques used in immunohematology are PCR-RFLP (Restriction Fragment Length Polymorphism) and PCR-SSP (Sequence-Specific-Primers). New methods have recently been developed for the study of twenty-eight of the twenty-nine erythrocyte systems whose sequence is known, such as, for example, PCR-ELISA (for RHD, RHCE, Kell, Duffy and Kidd antigenic systems), PCR real-time (for Kidd and Dombrock antigenic systems) and the micro-array technology. Although this development provides a fundamental support in immunohematology laboratories and in the field of transfusion medicine, most of the techniques currently available are unsuitable for wide-scale analysis, are relatively slow and require sophisticated and costly equipment.

Present-day new technologies appear to be aiming at automation and simplification and new instruments are modified to accelerate the process and maximize data production.

This latter concept is descriptive of multiplex flow cytometry dosages based on microspheres. By the conjugation of various purified Ag or oligonucleotide probes with distinct sets of fluorescent microspheres, extremely efficient analysis systems can be obtained, which allow numerous analytes to be taken from a single sample. The quantification exploits the multiparametric resolutive potential of flow cytometry and the capacity of processing systems of digital signals which process the thousands of fluorescent signals generated by the microspheres (Kellar, K. L., 2002; Kettman J R et al. 1998).

The microspheres consist of synthetic polymers and are characterized by a different fluorescence intensity. Various commercial sources of fluorescent microspheres are available such as Bangs Laboratories (Fishers, Ind.), Duke Scientific (Palo Alto, Calif.), Luminex Corporation (Austin, Tex.), Polysciences (Warrington, Pa.), Seradyn (Indianapolis, Ind.) and Spherotech (Libertyville, Ill.) which offer microspheres with various dimensions and fluorescence characteristics.

Luminex Corporation, for example, produces 100 microspheres with different fluorescence intensities created by the incorporation of various ratios of two fluorochromes which emit at different wave-lengths and are measured by means of different detectors (Fulton R. J. et al., 1997). A compact flow cytometer (Luminex 100) has been recently developed with two laser sources designed for the detection of microspheres and fluorescence quantification and an array of 100 coloured microspheres has been produced with fluoro-holes which emit at 658 and 712 nm after stimulation with a 635 nm red diode laser to complement the laser system of the cytometer. (Spain M. et al., 2001; Earley M C et al., 2002). This Multiple Analyte Profiling system (LabMAP™) has been used for the multiplex analysis of various single nucleotide polymorphisms (SNP) (Ye F. et al., 2001; Colinas R J et al., 2000; Dunbar S A et al., 2000). SNP are the most abundant variability source in the human genome and are consequently important for identifying the specific loci of particular pathologies or susceptibility of a person towards a particular disease or pharmacological therapy (Kellar K. L., 2003).

SNP also represent the molecular base of the polymorphisms of many antigenic systems such as, for example, the Kidd system, which is one of the main antigenic systems of human erythrocytes (Olives B. et al., 1997).

The Kidd erythrocyte system is defined by two specific alleles, $Jk^a$ and $Jk^b$ (Irshaid N M et al., 1998). The polymorphism $Jk^a/Jk^b$ consists in the substitution of a single nucleotide which determines an amino acidic substitution (Asp280Asn) at the level of the fourth extracellular loop of the Kidd glycoprotein. The Kidd locus ($Jk^a$, $Jk^b$ allele), localized on the 18q11-q12 chromosome, encodes an integral membrane glycoprotein which carries the urea through the erythrocyte membrane and which is expressed at the level of the endothelial cells of the vasa recta in the kidney (Irshaid N M et al., 1998). The hereditariness of $Jk^a$ and $Jk^b$ is codominant. There is also a Kidd "null" phenotype (Jk(a−b−)), which derives from different genetic alterations (Irshaid N M, 200 ref. 15), which makes erythrocytes resistant to 2 M urea lysis (Sidoux-Walter F., 2000; Lucien N. et al., 1998; 2002; Irshaid N M, 2002 ref. 13).

Anti-Kidd antibodies, often difficult to detect, represent a serious risk in the transfusion field. They have been involved in immediate hemolytic transfusions, serious and at times fatal, and in numerous delayed hemolytic transfusion reactions. These latter reactions can be serious and induce oligouria, renal problems which can sometimes lead to death. These specificities are often present together with others and have the characteristic of rapidly declining at low concentrations in the plasma and are therefore difficult to identify. It is estimated that about a third of delayed hemolytic reactions are caused by antibodies towards Kidd antigens.

Finally, the different frequency of the alleles of the Kidd gene in different populations can more easily lead to the production of specific antibodies if the donor and recipient belong to different ethnic groups.

When compatible donors are necessary for subjects with antibodies, the determination of the JK phenotype by means of serological methods becomes determinant in blood donors.

In view of what is specified above, there is an evident demand for new biotechnological instruments for the genomic typifying of erythrocyte systems which overcome the limits of the techniques currently adopted.

The authors of the present invention have now identified specific oligonucleotide probes which, when suitable modified, once conjugated to a solid support, such as for example an array of fluorescent microspheres, can be advantageously used for genomic typifying. The appropriate modification of the oligonucleotide probes is such as to allow their conjugation to the solid support.

In particular, the authors have developed a rapid and economic genomic erythrocyte typifying method and a relative diagnostic kit, which utilizes the probes according to the invention conjugated to fluorescent microspheres and which does not have the disadvantages of the known art.

The above method according to the invention is, in fact, based on a single amplification reaction followed by hybridization which makes it suitable for clinical typifying and also the typifying of populations. A single person can handle up to a maximum of 96 samples in a single operating session and two sessions can be carried out in the same day. By using the method according to the invention, for each determination, there is a considerable saving in terms of reagent costs and time (10 times lower with respect to other standard methods such as PCR).

From an applicative point of view, the method is particularly advantageous for the wide-scale typifying of blood samples as it facilitates the obtaining of typified or rare blood for alloimmunized patients and for subjects belonging to ethnic minorities.

More particularly, during the present study, after identifying the Kidd polymorphism at the level of the $Jk^a$ and $Jk^b$ alleles, the authors designed oligonucleotide probes capable of hybridizing specifically with the $Jk^a$ and $Jk^b$ alleles. These probes have advantages in terms of specificity and efficiency in the hybridization process.

The advantageous characteristics of the oligonucleotide probes identified by the authors of the present invention are as follows: the central localization of the polymorphism; the difference between the probes of a single nucleotide; a balanced ratio between the number of guanine and cytosine bases and the number of thymine and adenine bases to avoid circularization phenomena and/or the formation of loops.

The authors then developed and tested a rapid, accurate and efficient method for the determination of the polymorphism relating to the Kidd erythrocyte system. This method avails of the DNA target amplified via PCR by means of specific primers containing the SNP of the Kidd locus and the synthetic capture oligonucleotide probes according to the invention. The method according to the present invention was tested and validated on 200 subjects demonstrating that the method is sound in its capacity of accurately revealing the Kidd SNP and is tolerant with respect to the quantity, quality and source of material to be typified.

An object of the present invention therefore relates to oligonucleotide probes amino-modified at the 5' end characterized in that they have a sequence length ranging from 16 to 20 nucleotides, preferably 18 nucleotides, said sequence being characterized in that it comprises in the centre, the single nucleotide polymorphism (SNP) specific for the alleles belonging to a gene responsible for erythrocyte typifying and hybridizing with said polymorphic alleles. The above gene is selected from the group which consists of the following erythrocyte systems: Kidd (JK), Rh, MNS, Duffy (FY), Kell (KEL), Lutheran (LU), Diego (DI), YT, XG, Scianna (SC), Dombrock (DO), Colton (CO), Landsteiner-Wiener (LW), Hh (H), Gerbich (GE), Cromer (CROM), Indian (IN), John Milton Hagen (JMH) and Ii (I).

In a preferred embodiment of the present invention, the gene responsible for erythrocyte typifying is the Kidd gene and the amino-modified oligonucleotide probes (AmC12 modification at the 5' end) have the following sequences:

a) 5'-AmAGT AGA TGT CCT CAA ATG-3' b) 5'-AmAGT AGA TGT TCT CAA ATG-3' and the sequences complementary thereto.

More specifically, the probe a) is specific for the Jka allele of the Kidd gene, whereas the probe b) is specific for the JKb allele. The probes according to the present invention can be conjugated with a microparticle or set of microparticles marked with at least one fluorescent substance. The probes are preferably conjugated with a specific microsphere of the set supplied by Luminex Corporation. The genomic erythrocyte typifying preferably takes place by means of multiplex analysis with the Luminex LabMAP technique.

A further object of the present invention relates to microparticles, preferably microspheres, marked with at least one fluorescent substance having carboxylic groups on the surface, characterized in that they are conjugated with the probes as defined above. The fluorescent microspheres used are preferably those of Luminex.

Another object of the present invention relates to the use of the oligonucleotide probes defined above for the genomic erythrocyte identification and typifying of at least one single nucleotide polymorphism of the blood group in heterozygote and homozygote individuals. The genomic erythrocyte typifying relates to an erythrocyte system which can be selected from the group consisting of JK, Rh, MNS FY, KEL, LU, DI, YT, XG, SC, DO, CO, LW, H, GE, CROM, IN, JMH and I.

The present invention also relates to microparticles marked with at least one fluorescent substance having carboxylic groups on the surface, characterized in that they are conjugated with the probes as defined above.

Yet another object of the present invention relates to a method for the genomic erythrocyte identification and typifying of at least one single nucleotide polymorphism (SNP) of the blood group in heterozygote and homozygote individuals, comprising the following phases:

a) extraction of the DNA from a biological sample;

b) amplification via PCR of the gene comprising the single nucleotide polymorphism of the erythrocyte system to be analyzed by means of specific primers of which at least one is marked in 5' with biotin to obtain biotinylated PCR products (the biotinylation is preferably effected only at the level of the primer forward);

c) conjugation of the oligonucleotide probes as defined above with a microparticle or a set of microparticles marked with at least one fluorescent substance, the fluorescent microparticles are preferably of Luminex Corporation;

d) hybridization of the biotinylated PCR products of phase b) with the conjugated products of phase c) and detection with the addition of streptavidine-phycoerythrin;

e) detection of the fluorescence preferably by means of the LabMAP™ system.

In a preferred embodiment of the present invention, the single nucleotide polymorphism is the polymorphism of the Kidd blood group. The primers of phase b) preferably have the following sequences:

i) Forward 5'-CAT GCT GCC ATA GGA TCA TTGC-3' (preferably with BioTeg biotinylation at the 5'-end)

ii) Reverse 5'-GAG CCA GGA GGT GGG TTT GC-3';

and the oligonucleotide probes of phase c) have the following sequences:

```
iii)    5'-AmC12AGT AGA TGT CCT CAA ATG-3';

iv)     5'-AmC12AGT AGA TGT TCT CAA ATG-3';
``` or the sequences complementary thereto. AmC12 indicates the amino-modified 5' end followed by a chain with 12 carbon atoms as spacer element at the 5' end and the bases in bold type indicate the single nucleotide polymorphism.

The present invention also relates to a diagnostic kit for the genomic erythrocyte typifying of at least one single nucleotide polymorphism (SNP) of the blood group in heterozygote and homozygote individuals, comprising the following components:

a) a set of primers for amplification by PCR of the gene comprising the single nucleotide polymorphism of the erythrocyte system;

b) oligonucleotide probes as defined above, conjugated with a microparticle or a set of microparticles marked with at least one fluorescent substance, said probes being capable of hybridizing with said single nucleotide polymorphism.

In a preferred embodiment of the kit according to the invention, the single nucleotide polymorphism of the blood group is Kidd. In this specific case, the primers of phase a) of the kit according to the invention have the following sequences:

```
i)   Forward 5'-CAT GCT GCC ATA GGA TCA TTGC-3'
     (preferably with BioTeg biotinylation at the
     5'-end)

ii)  Reverse 5'-GAG CCA GGA GGT GGG TTT GC-3';
``` and the oligonucleotide probes of phase b) have the following sequences:

```
iii)    5'-AmC12AGT AGA TGT CCT CAA ATG-3';

iv)     5'-AmC12AGT AGA TGT TCT CAA ATG-3';
``` or the sequences complementary thereto.

The present invention will now be described for illustrative but non-limiting purposes, according to its preferred embodiment, with particular reference to the enclosed tables.

EXAMPLE 1

Genomic Typifying of the Kidd Erythrocyte System by Means of the Luminex System with Allele-Specific Oligonucleotide Probes Conjugated with an Array of Fluorescence Microspheres Materials and Methods Blood Samples 7 ml of peripheral blood of 200 healthy donors coming from the Blood Collection Centre of the Milan Polyclinic were collected in test-tubes containing a solution of EDTA as anticoagulant. The samples are preserved at −20° C. until the moment of treatment. Aliquots of 200 µl of whole blood were used for DNA extraction with a DNA purification kit (QIAamp, Qiagen, Mississauga, Ontario, Canada), according to the instructions of the producer. All the samples had a known serological typifying effected using standard agglutination methods for both of the antigens. The following known blood samples were tested: 50 samples Jk(a+b−); 50 samples Jk(a−b+) and 100 samples Jk(a+b+).

Reagents

The polystyrene microspheres COOH Xmap Multi-Analyte were purchased from Luminex Corporation (Austin, Tex., USA).

The microspheres (5.6 µm in diameter) have functional carboxylic surface groups for the chemical cross-link with different analytes which, for the purposes of the present invention, are oligodeoxyribonucleotide probes amino-modified (AmC12) at the 5' end.

The polystyrene microspheres were classified by flow cytometry thanks to the emission profile in the orange/red wave-length of each set of microspheres.

100 microspheres can be detected as each set incorporates colouring substances in an accurate ratio between each other which emit at different wave-lengths (red and infrared) allowing them to be distinguished. Each distinct set of microspheres, in fact, has exclusive marking characteristics and its own fluorescence intensity distribution which can be analyzed by the detection instrument. In this study, regions Nr. 64, 76, 72 and 73 were used. All the different sets of spheres numbered from 1 to 100 derive from the same starting material and differ only in the quantities of marking dyes present for the classification. The selection of the regions used was effected following the indications of the producer.

2-N-morpholine ethanesulfonic acid (MES), 1-ethyl-3-(3-dimethylaminopropyl) carbodi-imide hydrochloride (EDC), SAPE (100× stock 0.5 mg/ml Streptavidine-phycoerythrin) were obtained from Sigma, Pierce and One Lambda, Inc. respectively. The SDS (sodium dodecyl sulfate) and tetramethyl ammonium chloride (TMAC) and the washing buffer (SSPE-Triton X-100 Sigma) were purchased from Bio-RAD and Sigma, respectively.

Probe Design

All the oligonucleotides used for the covalent association with the microspheres were modified at the 5' end during the synthesis, using Amino-Modifier (AmC12-Qiagen Operon-Germania). The polymorphism of the groups $Jk^a$ and $Jk^b$ is localized at the centre of the probe sequence.

The probes used are 18 nucleotides long and were designed on the basis of the sequences filed having the filing numbers GeneBankAccession L36121 and PUBMED 7989337:

```
Probe Jka,
5'-AmC12AGT AGA TGT CCT CAA ATG-3'

Probe Jkb,
5'-AmC12AGT AGA TGT TCT CAA ATG-3'

Positive control probe (CP),
5'-AmC12AGG AAG CCA AGA TCT CAA-3';
```

Non-sense probe (NS), 5'-AmC12CGT GGA TTT CTT CAG AGG-3';

The positive control probe (CP) was designed on the basis of the sequence filed having the following filing numbers: GeneBankAccession AF046026 and PUBMED 9734652. The amplification was effected of the intron of 217 base pairs localized in the JK gene in nucleotide position 811-812. The intronic sequences are identical in all the samples regardless of the phenotype.

The negative control was designed by introducing random variations in the sequence of the specific probe for Jka.

Biotinylated oligonucleotides (ODN) were used, complementary to the alleles $Jk^a$, $Jk^b$, and to the controls for testing the conjugation efficiency of the oligonucleotide probes in turn modified at 5' with biotin. The fluorescent reagents were added and mixed to form a cocktail for multiplex analyses.

Conjugation of Oligonucleotide Probes with Microspheres

The four different oligonucleotide probes modified at 5' (AmC12) were conjugated in separate reactions with different classifications of carboxylated microspheres.

Each probe and set of carboxylated microspheres containing $7.5 \times 10^6$ microspheres were micro-centrifuged at 10,000 rpm for 2 minutes, the pellet was removed and resuspended in 75 μl of MES 0.1 M buffer, at pH 4.5. 0.3 nanomoles of amino-modified oligonucleotide probes were subsequently added to the mixture.

An aqueous solution of 1-ethyl-3-(3-dimethylaminopropyl)carbodi-imide HCl (EDC; 10 mg/ml) was then added to the mixture of microspheres/oligonucleotides and the resulting mixture was incubated at room temperature for 30 minutes in the dark. The addition of EDC and the incubation were repeated another time. After the total incubation of 1 hour, the microspheres were washed with 1.5 ml of Tween-20 at 0.02%. The washing solution was removed by micro-centrifugation, the washing was repeated with 1.5 ml of SDS at 0.1% and the final mixture was resuspended in 100 μl of TE, at pH 8 and kept in the dark at 4° C. Before use, the spheres were brought to room temperature for 5 minutes.

The conjugation efficiency was tested by hybridizing the conjugated microspheres with a molar excess of complementary biotinylated oligonucleotide (from 5 to 200 fentomoles) at a hybridization temperature of 45° C. Effective conjugation reactions produce microspheres with an average fluorescence intensity (MFI) ranging from 9000 to 15000.

PCR Amplification

The amplification comprises a segment of 380 bp which includes the polymorphism Jk in the nucleotide position 844 and the intronic region of 217 base pairs (bp) localized between the nucleotides 811-812.

The following primers were used for the PCR amplification, according to the instructions of the protocol described by Nidal M. Irshaid et al. (ref. 11 British Journal of Haematology 1998 102, 1010-1014), with modifications:

```
JK-781-F3 (forward)
5'-(BioTEG)-CAT GCT GCC ATA GGA TCA T-3'

JK-943-R3 (reverse)
5'-GAG CCA GGA GGT GGG TTT GC-3'.
```

The Forward primer was marked at the 5' end with biotin.

The PCR was effected with 1.2 pmol of primer, 50-100 ng of genomic DNA, 2 nmol of dNTPs and 0.5 U of Taq (Perkin Elmer), in the buffer supplied. The final reaction volume is equal to 20 μl.

The PCRGene Amp 9600 system (Perkin Elmer Cetus) was used for the thermal cycles under the following operating conditions per cycle: 10 minutes of initial denaturation of the DNA at 96° C., followed by 35 cycles at 94° C. for 30 seconds, 58° C. for 40 seconds, 72° C. for 40 seconds, with a final elongation phase at 72° C. for 2 minutes. The DNA fragments obtained have a length equal to 380 base pairs and were analyzed and verified by electrophoresis on agarose gel at 2%.

Hybridization

After the PCR amplification, 4 μl of each reaction were transferred to micro-titration plates with 96 cavities and diluted with 17 μl of TE and denatured under heat at 99° C. for 10 minutes in a preheated Thermal Cycler. The denaturation phase was blocked with a lump of ice. The hybridization of the biotinylated PCR products with the four classifications of spheres conjugated with ODN, was effected in a buffer containing tetramethylammonium chloride (TMAC) (TMAC 1.5×4.5 M, SDS 0.15%, Tris-HCl 75 mM pH 8, EDTA 6 mM pH 8).

33 μl of a hybridization solution containing a mixture of 5,000 spheres of each set conjugated with the probe in a total reaction volume of 50 μl, were added to each sample. The samples were mixed and immediately transferred to the amplifier plate preheated to 45° C. The hybridization was carried out at 45° C. for 15 minutes and the samples were diluted to 150 μl with 100 μl of washing buffer (6×SSPET).

The washing phases were carried out at room temperature by means of centrifugation (2,800 rpm for 5 minutes) with the elimination of the supernatant using a vacuum micropump. The samples were washed three times.

The spheres were incubated for 5 minutes at 45° C. with 50 μl of a fresh solution of 1×SAPE (0.5 mg/l streptavidine-R-phycoerythrin) in 1×TMAC (TMAC 3M, SDS 0.11, Tris-HCl 50 mM, pH 8, EDTA 4 mM pH 8). At the end of the incubation, 100 μl of washing buffer were rapidly added to each cavity, the spheres were then pelletized by centrifugation and the supernatant removed. Each sample was subsequently resuspended in 80 μl of washing buffer (Sheath Fluid supplied by Luminex Corporation). In order to have better results, it is better to read the samples as soon as possible. If the plate cannot be read immediately, the samples can be preserved at 4° C. in the dark for up to a maximum of 24 hours.

Data Acquisition and Analysis

The samples were analyzed using a LAB Scan™100 (Luminex Corporation, Austin, Tex.).

The instrument is equipped with two laser sources of which a 635 nm diode laser to stimulate the fluorochromes classified in red and infrared and a 532 laser to stimulate the orange phycoerythrin (PE) reporter fluorochrome.

Each set of spheres has a single fluorescence intensity distribution which can be read from the instrument.

Two parameters, the fluorescence count and intensity (IF) were monitored for each data acquisition.

The count should be higher than 100. The fluorescence intensity (IF) represents a PE signal revealed inside the spheres counted. The IF for the positive control probe indicates the optimum sample quantity and/or quality and the correct activation of all the hybridization phases.

The acquisition for each single sample should normally be completed in less than a minute.

Data Calculation

The fluorescence intensity (MFI—median fluorescence intensity) generated by the Luminex software represents the MFI of each microsphere (or probe linked to the microsphere) for each sample. The positive percentage value for each specific probe is calculated as the ratio between the MFI value of the Jka or Jkb probe and the MFI value of the positive control probe multiplied by 100 according to the following formula:

Positive value %=100×$FI$($n$. probe)–$FI$(negative control probe)/$FI$(positive control probe)–$FI$(negative control probe)

The MFI values are used in the formula, from each of which the MFI value generated from the negative control probe for each sample is subtracted.

The positive reaction is defined as the percentage of positive values for the probe higher than the pre-established cutoff value for the probe itself, the negative reaction as the percentage of positive values lower than the cutoff value.

Positive Control

From the data analysis of 200 samples tested, the MFI value of the positive control, corrected by the negative control value (MFI positive control probe-MFI negative control probe) proves to have an average MFI having a value of 685.5 with a standard deviation of 179.79.

Samples having a positive control fluorescence signal (MFI) which is higher or equal to a value of 506, are considered reliable.

Cutoff Value

The cutoff value was pre-established for each probe (Jka and Jkb) using a panel of 200 known serological typifying samples of which 100 samples with a heterozygote asset Jk(a+b+) and 50 samples with a homozygote asset, respectively, for each allele.

The cutoff value for each allele was obtained from the difference in the lowest percentage value (calculated as described above) obtained in positive samples for the allele considered and the highest percentage value obtained in negative samples for the allele considered. The half value thus obtained represents the percentage value which defines the reference cutoff for the two alleles considered Jka and Jkb.

The following cutoff values were obtained from the data analysis (see tables 1, 2 and 3 enclosed):

the cutoff value for the probe Jka proves to be equal to 10%; the lowest percentage value in positive samples for the allele Jka (see table 1) proves to be equal to 29.5%; the highest percentage value in negative samples (see table 3) proves to be equal to 9.8%;

the cutoff value for the probe Jkb proves to be equal to 33%; the lowest percentage value (V %) in positive samples for the allele $Jk^b$ (see table 1) proves to be equal to 95.1%; the highest percentage value in negative samples (see table 2) proves to be equal to 29.9%

TABLE 1

Heterozygote samples Jk (a+ b+)

| Nr. | | MFI probe Jka | | MFI probe Jkb | | MFI probe CP | CN | V % probe Jka | V % probe Jkb |
|---|---|---|---|---|---|---|---|---|---|
| 1 | 348 | 330 | 942.5 | 924.5 | 785.5 | 767.5 | 18 | 43.0 | 120.5 |
| 2 | 368 | 352 | 904 | 888 | 704 | 688 | 16 | 51.2 | 129.1 |
| 3 | 325 | 295.5 | 737 | 707.5 | 625 | 595.5 | 29.5 | 49.6 | 118.8 |
| 4 | 364.5 | 330.5 | 866.5 | 832.5 | 712.5 | 678.5 | 34 | 48.7 | 122.7 |
| 5 | 356 | 334.5 | 953 | 931.5 | 765.5 | 744 | 21.5 | 45.0 | 125.2 |
| 6 | 337 | 324 | 855.5 | 842.5 | 707.5 | 694.5 | 13 | 46.7 | 121.3 |
| 7 | 417 | 346 | 988.5 | 917.5 | 794 | 723 | 71 | 47.9 | 126.9 |
| 8 | 368.5 | 349.5 | 892 | 873 | 711.5 | 692.5 | 19 | 50.5 | 126.1 |
| 9 | 211 | 162 | 563 | 514 | 389 | 340 | 49 | 47.6 | 151.2 |
| 10 | 528 | 517 | 1266 | 1255 | 1039 | 1028 | 11 | 50.3 | 122.1 |
| 11 | 424 | 367 | 1004 | 947 | 827 | 770 | 57 | 47.7 | 123.0 |
| 12 | 217.5 | 159.5 | 358.5 | 300.5 | 301 | 243 | 58 | 65.6 | 123.7 |
| 13 | 176 | 125 | 446 | 395 | 285 | 234 | 51 | 53.4 | 168.8 |
| 14 | 244.5 | 185.5 | 624 | 565 | 505 | 446 | 59 | 41.6 | 126.7 |
| 15 | 402.5 | 341.5 | 979.5 | 918.5 | 744 | 683 | 61 | 50.0 | 134.5 |
| 16 | 367 | 320 | 961.5 | 914.5 | 712 | 665 | 47 | 48.1 | 137.5 |
| 17 | 381.5 | 313 | 1148 | 1079.5 | 1130 | 1061.5 | 68.5 | 29.5 | 101.7 |
| 18 | 337 | 289.5 | 837.5 | 790 | 727.5 | 680 | 47.5 | 42.6 | 116.2 |
| 19 | 425 | 331.5 | 838.5 | 745 | 790 | 696.5 | 93.5 | 47.6 | 107.0 |
| 20 | 353.5 | 284.5 | 805 | 736 | 747 | 678 | 69 | 42.0 | 108.6 |
| 21 | 441 | 399 | 864.5 | 822.5 | 633.5 | 591.5 | 42 | 67.5 | 139.1 |
| 22 | 356 | 305 | 886 | 835 | 713.5 | 662.5 | 51 | 46.0 | 126.0 |
| 23 | 322 | 291 | 877 | 776 | 846 | 745 | 31 | 39.1 | 113.6 |
| 24 | 340 | 301 | 876.5 | 837.5 | 753.5 | 714.5 | 39 | 42.1 | 117.2 |
| 25 | 350.5 | 309 | 852 | 810.5 | 692 | 650.5 | 41.5 | 47.5 | 124.6 |
| 26 | 348 | 319 | 856.5 | 827.5 | 724 | 695 | 29 | 45.9 | 119.1 |
| 27 | 318 | 270 | 796 | 748 | 567.5 | 519.5 | 48 | 52.0 | 144.0 |
| 28 | 408 | 319 | 897 | 808 | 798 | 709 | 89 | 45.0 | 114.0 |
| 29 | 388 | 350 | 891.5 | 853.5 | 627 | 589 | 38 | 59.4 | 144.9 |
| 30 | 256 | 211 | 618.5 | 573.5 | 580 | 535 | 45 | 39.4 | 107.2 |
| 31 | 404 | 341 | 898.5 | 835.5 | 752 | 689 | 63 | 49.5 | 121.3 |
| 32 | 408.5 | 354.5 | 808.5 | 754.5 | 558 | 504 | 54 | 70.3 | 149.7 |
| 33 | 409 | 363 | 972.5 | 926.5 | 785 | 739 | 46 | 49.1 | 125.4 |
| 34 | 448.5 | 410 | 893 | 854.5 | 641 | 602.5 | 38.5 | 68.0 | 141.8 |
| 35 | 524.5 | 446.5 | 1044.5 | 966.5 | 832.5 | 754.5 | 78 | 59.2 | 128.1 |
| 36 | 582.5 | 494.5 | 1291 | 1203 | 1089 | 1001 | 88 | 49.4 | 120.2 |
| 37 | 654.5 | 571.5 | 1395 | 1312 | 1073 | 990 | 83 | 57.7 | 132.5 |
| 38 | 581 | 518 | 1219 | 1156 | 1036 | 973 | 63 | 53.2 | 118.8 |
| 39 | 659 | 548 | 1317.5 | 1206.5 | 1047 | 936 | 111 | 58.5 | 128.9 |
| 40 | 526.5 | 410.5 | 1009.5 | 893.5 | 958 | 842 | 116 | 48.8 | 106.1 |
| 41 | 588 | 506 | 1185.5 | 1103.5 | 985 | 903 | 82 | 56.0 | 122.2 |
| 42 | 520 | 428 | 1015 | 923 | 1002 | 910 | 92 | 47.0 | 101.4 |
| 43 | 644 | 523 | 1383 | 1262 | 1257 | 1136 | 121 | 46.0 | 111.1 |
| 44 | 393 | 271.5 | 1190 | 1068.5 | 1000 | 878.5 | 121.5 | 30.9 | 121.6 |
| 45 | 597 | 431 | 1175 | 1009 | 951 | 785 | 166 | 54.9 | 128.5 |
| 46 | 682 | 526 | 1056 | 900 | 918 | 762 | 156 | 69.0 | 118.1 |
| 47 | 553 | 457 | 1176 | 1080 | 953 | 857 | 96 | 53.3 | 126.0 |
| 48 | 519 | 370.5 | 1191 | 1042.5 | 937 | 788.5 | 148.5 | 47.0 | 132.2 |
| 49 | 492 | 398 | 947 | 853 | 835 | 741 | 94 | 53.7 | 115.1 |
| 50 | 593 | 497.5 | 1254 | 1158.5 | 1110 | 1014.5 | 95.5 | 49.0 | 114.2 |
| 51 | 563 | 503 | 1167 | 1107 | 980.5 | 920.5 | 60 | 54.6 | 120.3 |
| 52 | 565 | 505 | 1155 | 1095 | 1011.5 | 951.5 | 60 | 53.1 | 115.1 |
| 53 | 375 | 284.5 | 854.5 | 764 | 666 | 575.5 | 90.5 | 49.4 | 132.8 |

TABLE 1-continued

Heterozygote samples Jk (a+ b+)

| Nr. | MFI probe Jka | | MFI probe Jkb | | MFI probe CP | CN | V % probe Jka | V % probe Jkb |
|---|---|---|---|---|---|---|---|---|
| 54 | 395 | 281 | 935.5 | 821.5 | 759 | 645 | 114 | 43.6 | 127.4 |
| 55 | 397 | 296.5 | 916.5 | 816 | 710 | 609.5 | 100.5 | 48.6 | 133.9 |
| 56 | 330.5 | 265.5 | 807 | 742 | 697 | 632 | 65 | 42.0 | 117.4 |
| 57 | 341 | 265 | 839 | 763 | 679 | 603 | 76 | 43.9 | 126.5 |
| 58 | 338.5 | 311.5 | 828.5 | 801.5 | 658 | 631 | 27 | 49.4 | 127.0 |
| 59 | 631 | 387.5 | 1045 | 801.5 | 769 | 525.5 | 243.5 | 73.7 | 152.5 |
| 60 | 392 | 260.5 | 805.5 | 674 | 661 | 529.5 | 131.5 | 49.2 | 127.3 |
| 61 | 368 | 226.5 | 832.5 | 691 | 653 | 511.5 | 141.5 | 44.3 | 135.1 |
| 62 | 467 | 296 | 945.5 | 774.5 | 696.5 | 525.5 | 171 | 56.3 | 147.4 |
| 63 | 504.5 | 333.5 | 1035 | 864 | 893 | 722 | 171 | 46.2 | 119.7 |
| 64 | 434 | 312.5 | 973 | 851.5 | 713 | 591.5 | 121.5 | 52.8 | 144.0 |
| 65 | 331.5 | 281.5 | 852 | 802 | 711 | 661 | 50 | 42.6 | 121.3 |
| 66 | 433.5 | 391 | 735 | 692.5 | 641.5 | 599 | 42.5 | 65.3 | 115.6 |
| 67 | 354.5 | 229.5 | 933.5 | 878.5 | 747 | 692 | 55 | 43.3 | 127.0 |
| 68 | 385 | 336 | 939 | 890 | 759 | 710 | 49 | 47.3 | 125.4 |
| 69 | 411 | 353.5 | 950 | 892.5 | 741.5 | 684 | 57.5 | 51.7 | 130.5 |
| 70 | 418.5 | 342.5 | 920 | 844 | 754 | 678 | 76 | 50.5 | 124.5 |
| 71 | 396 | 322 | 934 | 860 | 742 | 668 | 74 | 48.2 | 128.7 |
| 72 | 347 | 296 | 863 | 812 | 729 | 678 | 51 | 43.7 | 119.9 |
| 73 | 344 | 310 | 865 | 831 | 722 | 688 | 34 | 45.1 | 120.8 |
| 74 | 351 | 308 | 865.5 | 822.5 | 744.5 | 701.5 | 43 | 43.9 | 117.2 |
| 75 | 358 | 326 | 898.5 | 866.5 | 730 | 698 | 32 | 46.7 | 124.1 |
| 76 | 323 | 284 | 848.5 | 809.5 | 684.5 | 645.5 | 39 | 44.0 | 125.4 |
| 77 | 385 | 339.5 | 972 | 926.5 | 710 | 664.5 | 45.5 | 51.1 | 139.4 |
| 78 | 495 | 406 | 1032.5 | 943.5 | 816 | 727 | 89 | 55.8 | 129.8 |
| 79 | 389.5 | 297.5 | 706.5 | 614.5 | 535.5 | 443.5 | 92 | 67.1 | 138.6 |
| 80 | 399.5 | 305.5 | 903.5 | 809.5 | 685.5 | 591.5 | 94 | 51.6 | 136.9 |
| 81 | 405.5 | 310.5 | 852 | 757 | 718 | 623 | 95 | 49.8 | 121.5 |
| 82 | 414 | 328 | 971 | 885 | 809 | 723 | 86 | 45.4 | 122.4 |
| 83 | 383.5 | 307.5 | 963 | 887 | 760.5 | 684.5 | 76 | 44.9 | 129.6 |
| 84 | 425 | 345 | 794.5 | 714.5 | 713 | 633 | 80 | 54.5 | 112.9 |
| 85 | 368 | 290.5 | 899 | 821.5 | 804.5 | 727 | 77.5 | 40.0 | 113.0 |
| 86 | 395 | 306.5 | 639 | 550.5 | 480 | 391.5 | 88.5 | 78.3 | 140.6 |
| 87 | 415 | 332 | 775 | 692 | 687.5 | 604.5 | 83 | 54.9 | 114.5 |
| 88 | 402 | 318 | 699.5 | 615.5 | 674 | 590 | 84 | 53.9 | 104.3 |
| 89 | 365 | 277 | 876 | 788 | 714 | 626 | 88 | 44.2 | 125.9 |
| 90 | 422.5 | 342.5 | 921 | 841 | 779.5 | 699.5 | 80 | 49.0 | 120.2 |
| 91 | 440 | 359 | 903 | 822 | 729.5 | 648.5 | 81 | 55.4 | 126.8 |
| 92 | 430 | 333 | 782 | 685 | 788.5 | 691.5 | 97 | 48.2 | 99.1 |
| 93 | 369.5 | 250.5 | 675 | 556 | 518 | 399 | 119 | 62.8 | 139.3 |
| 94 | 416 | 320.5 | 836 | 740.5 | 874 | 778.5 | 95.5 | 41.2 | 95.1 |
| 95 | 430 | 297 | 942 | 809 | 745 | 612 | 133 | 48.5 | 132.2 |
| 96 | 456.5 | 391.5 | 755 | 690 | 516 | 451 | 65 | 86.8 | 153.0 |
| 97 | 427.5 | 354.5 | 852 | 779 | 553.5 | 480.5 | 73 | 73.8 | 162.1 |
| 98 | 402.5 | 348.5 | 909 | 855 | 672 | 618 | 54 | 56.4 | 138.3 |
| 99 | 379.5 | 338.5 | 927 | 886 | 723 | 682 | 41 | 49.6 | 129.9 |
| 100 | 431.5 | 386.5 | 977 | 932 | 829.5 | 784.5 | 45 | 49.3 | 118.8 |

TABLE 2

Samples Jk (a+ b−)

| Nr | MFI probe Jka | MFI probe Jkb | MFI probe CP | V % probe Jka | V % probe Jkb |
|---|---|---|---|---|---|
| 1 | 591 | 95 | 863.5 | 68.4 | 11.0 |
| 2 | 590 | 108 | 958 | 61.6 | 11.3 |
| 3 | 556.5 | 74.5 | 754 | 73.8 | 9.9 |
| 4 | 556 | 84 | 835 | 66.6 | 10.1 |
| 5 | 550.5 | 79 | 815.5 | 67.5 | 9.7 |
| 6 | 495 | 84.5 | 792 | 62.5 | 10.7 |
| 7 | 591 | 111 | 892.5 | 66.2 | 12.4 |
| 8 | 547 | 79 | 755 | 72.5 | 10.5 |
| 9 | 610 | 99 | 920 | 66.3 | 10.8 |
| 10 | 475 | 85 | 774 | 61.4 | 11.0 |
| 11 | 510 | 93 | 736.5 | 69.2 | 12.6 |
| 12 | 523 | 102 | 761.5 | 68.7 | 13.4 |
| 13 | 504 | 87 | 732 | 68.9 | 11.9 |
| 14 | 463 | 73 | 697.5 | 66.4 | 10.5 |
| 15 | 559 | 95 | 786.5 | 71.1 | 12.1 |
| 16 | 545.5 | 114 | 748.5 | 72.9 | 15.2 |
| 17 | 556 | 127 | 1190.5 | 46.7 | 10.7 |
| 18 | 777 | 166.5 | 1524 | 51.0 | 10.9 |
| 19 | 397 | 68.5 | 611 | 65.0 | 11.2 |
| 20 | 743 | 130 | 978 | 76.0 | 13.3 |
| 21 | 811.5 | 154.5 | 1148 | 70.7 | 13.5 |
| 22 | 766.5 | 142.5 | 1074.5 | 71.3 | 13.3 |
| 23 | 687 | 116 | 982.5 | 69.9 | 11.8 |
| 24 | 729 | 137 | 1093 | 66.7 | 12.5 |
| 25 | 666 | 127 | 1044 | 63.8 | 12.2 |
| 26 | 231 | 63.5 | 367 | 62.9 | 17.3 |
| 27 | 647 | 105 | 547.5 | 123.1 | 19.2 |
| 28 | 675.5 | 120 | 889 | 76.0 | 13.5 |
| 29 | 454 | 97 | 763 | 59.5 | 12.7 |
| 30 | 551 | 90.5 | 774 | 71.2 | 11.7 |

TABLE 2-continued

| Samples Jk (a+ b−) | | MFI probe Jkb | MFI probe CP | V % probe Jka | V % probe Jkb |
|---|---|---|---|---|---|
| Nr | MFI probe Jka | | | | |
| 31 | 434.5 | 80 | 660.5 | 65.8 | 12.1 |
| 32 | 468.5 | 110.5 | 597 | 78.5 | 18.5 |
| 33 | 420 | 71.5 | 566 | 74.2 | 12.6 |
| 34 | 496.5 | 87 | 639.5 | 77.6 | 13.6 |
| 35 | 511.5 | 92 | 809.5 | 63.2 | 11.4 |
| 36 | 594.5 | 88.5 | 802.5 | 74.1 | 11.0 |
| 37 | 434.5 | 113 | 710 | 61.2 | 15.9 |
| 38 | 688 | 86 | 649 | 106.0 | 13.3 |
| 39 | 566.5 | 92 | 798 | 71.0 | 11.5 |
| 40 | 574.5 | 239 | 800 | 71.8 | 29.9 |
| 41 | 584 | 87 | 588 | 99.3 | 14.8 |
| 42 | 592 | 102 | 816 | 72.5 | 12.5 |
| 43 | 533 | 108 | 852 | 62.6 | 12.7 |
| 44 | 617 | 108 | 888.5 | 69.4 | 12.2 |
| 45 | 487 | 66 | 469 | 103.8 | 14.1 |
| 46 | 566 | 100 | 784.5 | 72.1 | 12.7 |
| 47 | 625.5 | 116.5 | 857.5 | 72.9 | 13.6 |
| 48 | 625 | 107 | 877.5 | 71.2 | 12.2 |
| 49 | 572.5 | 66 | 563 | 101.7 | 11.7 |
| 50 | 553.5 | 75 | 567.5 | 97.5 | 13.2 |

TABLE 3

| Samples Jk (a− b+) | | MFI probe Jkb | MFI probe CP | V % probe Jka | V % probe Jkb |
|---|---|---|---|---|---|
| Nr | MFI probe Jka | | | | |
| 1 | 33.5 | 989 | 613 | 5.5 | 161.3 |
| 2 | 6 | 1212 | 537 | 1.1 | 225.7 |
| 3 | −5 | 1188 | 531 | 0.9 | 223.7 |
| 4 | 14.5 | 1173 | 553 | 2.6 | 212.1 |
| 5 | 23.5 | 1255.5 | 717 | 3.3 | 175.1 |
| 6 | 22 | 1445 | 694 | 3.2 | 208.2 |
| 7 | 24 | 1319 | 586 | 4.1 | 225.1 |
| 8 | 29 | 1590 | 692.5 | 4.2 | 229.6 |
| 9 | 28 | 1226 | 576.5 | 4.9 | 212.7 |
| 10 | 32 | 1318.5 | 624 | 5.1 | 211.3 |
| 11 | 36 | 1236.5 | 645 | 5.6 | 191.7 |
| 12 | 35 | 1377 | 634.5 | 5.5 | 217.0 |
| 13 | 30.5 | 1241 | 600 | 5.1 | 206.8 |
| 14 | 26.5 | 1149 | 621.5 | 4.3 | 184.9 |
| 15 | 25.5 | 1214 | 548 | 4.7 | 221.5 |
| 16 | 26 | 1186 | 504 | 5.2 | 235.3 |
| 17 | 12 | 507 | 243.5 | 4.9 | 208.2 |
| 18 | 12 | 741.5 | 393.5 | 3.0 | 188.4 |
| 19 | 8 | 1029.5 | 474.5 | 1.7 | 217.0 |
| 20 | 49 | 1502 | 713 | 6.9 | 210.7 |
| 21 | 46 | 1226.5 | 591.5 | 7.8 | 207.4 |
| 22 | 30.5 | 1690.5 | 851 | 3.6 | 198.6 |
| 23 | 24.5 | 1365 | 664 | 3.7 | 205.6 |
| 24 | 53 | 1493 | 738.5 | 7.2 | 202.2 |
| 25 | 36 | 1758.5 | 964.5 | 3.7 | 182.3 |
| 26 | 15 | 1235.5 | 573 | 2.6 | 215.6 |
| 27 | 21.5 | 1187 | 533.5 | 4.0 | 222.5 |
| 28 | 14.5 | 1166 | 395.5 | 3.7 | 294.8 |
| 29 | 15 | 1153 | 498 | 3.0 | 231.5 |
| 30 | 10 | 1222.5 | 592.5 | 1.7 | 206.3 |
| 31 | 28 | 1191 | 516 | 5.4 | 230.8 |
| 32 | 13.5 | 1077.5 | 416 | 3.2 | 259.0 |
| 33 | 12 | 1019 | 462 | 2.6 | 220.6 |
| 34 | 28 | 1314 | 500 | 5.6 | 262.8 |
| 35 | 15.5 | 1241.5 | 542.5 | 2.9 | 228.8 |
| 36 | 18.5 | 1227 | 543.5 | 3.4 | 225.8 |
| 37 | 20 | 1089.5 | 573 | 3.5 | 190.1 |
| 38 | 22 | 1413 | 568.5 | 3.9 | 248.5 |
| 39 | 21 | 1100.5 | 376 | 5.6 | 292.7 |
| 40 | 17.5 | 1375.5 | 609.5 | 2.9 | 225.7 |
| 41 | 27 | 1427.5 | 631 | 4.3 | 226.2 |
| 42 | 26 | 1475.5 | 683 | 3.8 | 216.0 |
| 43 | 20.5 | 1356.5 | 609.5 | 3.4 | 222.6 |
| 44 | 22 | 1198 | 611 | 3.6 | 196.1 |
| 45 | 22 | 1436.5 | 644.5 | 3.4 | 222.9 |

TABLE 3-continued

| Samples Jk (a− b+) | | MFI probe Jkb | MFI probe CP | V % probe Jka | V % probe Jkb |
|---|---|---|---|---|---|
| Nr | MFI probe Jka | | | | |
| 46 | 23 | 1290 | 553 | 4.2 | 233.3 |
| 47 | 34 | 1101 | 363 | 9.4 | 303.3 |
| 48 | 18.5 | 1539.5 | 558 | 3.3 | 275.9 |
| 49 | 46 | 1321 | 613 | 7.5 | 215.5 |
| 50 | 59.5 | 1506.5 | 605.5 | 9.8 | 248.8 |

BIBLIOGRAPHY

Colinas R J, Bellisario R, Pass K A. Clinical Chemistry 2000; 46 n. 7: 996-998.

Dunbar S A, Jacobson J W. Clinical Chemistry 2000; 46 n. 9: 1498-1500.

Earley M C, Vogt R F, Shapiro H M, Mandy F F, Kellar K L, Bellisario R, Pass K A, Marti G E, Stewart C C, Hannon W H. Cytometry (Clinical Cytometry) 2002; 50: 239-242.

Keller K L, Iannone M A. Exp. Hematol. 2002; 30:1227-1237.

Kellar K L. Journal of Clinical Ligand Assay 2003; 26 n. 2: 82-92.

Iannone M A, Taylor J D, Chen J. Li M S, Rivers P, Slentz-Kesler K A, Weiner M. Cytometry 2000; 39: 131-140.

Fulton J R, McDade R L, Smith P L, Kienker L J, Kettman J R. Clinical Chemistry 1997; 43 n. 9: 1749-1756.

Taylor J D, Briley D, Nguyen Q, Long K, Iannone M A, Li S, Ye F, Afshari A, Lai E, Wagner M, Chen J, Weiner M P. Biotechniques 2001; 30: 661-669.

Armstrong B, Stewart M, Mazumder A. Cytometry 2000; 40: 102-108.

Kettman J R, Davies T, Chandler D, Oliver K G, Fulton R J. Cytometry 1998; 33: 234-243.

Defoort J P, Martin M, Casano B, Prato S, Camilla C, Fert V. Journal of Clinical Microbiology 2000; 38 n. 3: 1066-1071.

Irshaid N M, Thuresson B, Olsson M L. British Journal of Haematology 1998; 102: 1010-1014.

Lucien N, Chiarori J, Cartron J P, Bailly. Blood 2002; 99: 1079-1081.

Irshaid N M, Eicher N I, Hustinx H, Poole J, Olsson M L. British Journal of Haematology 2002; 116: 445-453.

Sidoux-Walter F, Lucine N, Nissinen Riikka, Sistonen P, Henry S, Moulds J, Cartron J P, Bailly P. Blood 2000; 96 n. 4; 1567-1573.

Irshaid N M, Henry S M, Olsson M L. Transfusion 2000; 40: 69-74.

Lucien N, Sidoux W F, Olives B, Moulds J, Le Pennec P Y, Cartron J P, Bailly P. Issue 1998; 273 n. 21: 12973-12980.

Olives B, Merriman M, Bailly P, Bain S, Barnett A, Todd J, Cartron J P, Merriman T. Human Molecular Genetics 1997; 6 n. 7: 1017-1020.

Hessner M J, Pircon R A, Johnson S T, Luhm R A. Prenatal Diagnosis 1998; 18: 1225-1231.

Spain M, Jacobson J. Amer Genomics/Proteomics Technol. 2001; 47: 1241-1256

Ye F, Li M-S, Taylor J D. Hum. Mutat 2001; 17: 305-316.

The invention claimed is:

1. Oligonucleotide probes amino-modified at the 5' end having a sequence length ranging from 16 to 20 nucleotides, said sequence being characterized in that it comprises, at the centre, the single nucleotide polymorphism (SNP) of the Kidd erythrocyte system which is specific for the alleleic variants of the gene coding for said polymorphism and said oligonucleotide probes hybridizing with said alleles, wherein said gene is the Kidd gene said probes having the sequence: (a) 5'-AmC12AGT AGA TGT CCT CAA ATG-3' or (b) 5'-AmC12AGT AGA TGT TCT CAA ATG-3'.

2. The probes according to claim 1, said probes are conjugated with a microparticle or set of microparticles marked with at least one fluorescent substance.

3. Use of the oligonucleotide probes as defined in claim 1 for the identification and genomic erythrocyte typing of at least one single nucleotide polymorphism of the blood group in heterozygote and homozygote individuals.

4. Microparticles marked with at least one fluorescent substance having carboxylic groups on the surface, characterized in that they are conjugated with the probes as defined in claim 1.

5. A method for the identification of and typing for at least one single nucleotide polymorphism (SNP) of the blood group in heterozygote and homozygote individuals, comprising the following phases: a) DNA extraction from a biological sample; b) amplification via PCR of the gene fragment comprising the single nucleotide polymorphism of the Kidd erythrocyte system to be analyzed by means of specific primers of which at least one is marked at the 5' end with biotin to obtain biotinylated PCR products; c) conjugation of an oligonucleotide probe, having the sequence (i) 5'-AmC12AGT AGA TGT CCT CAA ATG-3' or (ii) 5'-AmC12AGT AGA TGT TCT CAA ATG-3' with a microparticle or a set of micro-particles marked with at least one fluorescent substance; d) hybridization of the biotinylated PCR products of phase b) with the conjugated products of phase c) and detection with the addition of streptavidine-phycoerythrin,] and e) detection of the fluorescence.

6. The method according to claim 5, wherein the primers of phase b) have the following sequences: i) Forward 5'-CAT GCT GCC ATA GGA TCA TTGC-3' upsilon and Reverse 5'-GAG CCA GGA GGT GGG TTT GC-3'.

7. The method according to claim 5, wherein the primer I) is biotinylated at the 5' end.

8. A diagnostic kit for the identification and genomic erythrocyte typifying of at least one single nucleotide polymorphism (SNP) of the Kidd erythrocyte system of the blood group in heterozygote and homozygote individuals, comprising the following components: a) a set of primers for amplification by PCR of the gene comprising the single nucleotide polymorphism of the Kidd erythrocyte system; and b) oligonucleotide probes having the sequences (iii) 5'-AmC12AGT AGA TGT CCT CAA ATG-3' or (iv) 5'-AmC12AGT AGA TGT TCT CAA ATG-3', conjugated with a microparticle or a set of microparticles marked with at least one fluorescent substance, said probes being capable of hybridizing with said single nucleotide polymorphism.

9. The diagnostic kit according to claim 8, wherein the primers of have the following sequences: i) Forward 5'-CAT GCT GCC ATA GGA TCA TTGC-3' and Reverse 5'-GAG CCA GGA GGT GGG TTT GC-3'.

10. The diagnostic kit according to claim 9 wherein the primer i) is biotinylated at the 5'.

* * * * *

SEQUENCE LISTING

<160> NUMBER OF SEQ ID NOS: 6

<210> SEQ ID NO 1
<211> LENGTH: 19
<212> TYPE: DNA
<213> ORGANISM: Artificial
<220> FEATURE:
<223> OTHER INFORMATION: Amino-modified oligonucleotide probe specific
      for Jka allele of the kidd gene
<220> FEATURE:
<221> NAME/KEY: misc-feature
<222> LOCATION: (1)..(1)
<223> OTHER INFORMATION: n indicates the aminomodified 5' end followed
      by a chain with 12 carbon atoms as spacer element at the 5' end

<400> SEQUENCE: 1
nagtagatgt cctcaaatg                                                  19

<210> SEQ ID NO 2
<211> LENGTH: 19
<212> TYPE: DNA
<213> ORGANISM: Artificial
<220> FEATURE:
<223> OTHER INFORMATION: Amino-modified oligonucleotide probe specific
      for Jkb allele of the kidd gene
<220> FEATURE:
<221> NAME/KEY: misc-feature
<222> LOCATION: (1)..(1)
<223> OTHER INFORMATION: n indicates the amino-modified 5'end followed
      by a chain with 12 carbon atoms as spacer element at the 5'end

<400> SEQUENCE: 2
nagtagatgt tctcaaatg                                                  19

<210> SEQ ID NO 3
<211> LENGTH: 22
<212> TYPE: DNA
<213> ORGANISM: Artificial
<220> FEATURE:
<223> OTHER INFORMATION: Forward primer

<400> SEQUENCE: 3
catgctgcca taggatcatt gc                                              22

<210> SEQ ID NO 4
<211> LENGTH: 20
<212> TYPE: DNA
<213> ORGANISM: Artificial
<220> FEATURE:
<223> OTHER INFORMATION: Reverse primer

<400> SEQUENCE: 4
gagccaggag gtgggtttgc                                                 20

<210> SEQ ID NO 5
<211> LENGTH: 19
<212> TYPE: DNA
<213> ORGANISM: Artificial
<220> FEATURE:
<223> OTHER INFORMATION: Positive control probe
<220> FEATURE:
<221> NAME/KEY: misc_feature
<222> LOCATION: (1)..(1)
<223> OTHER INFORMATION: n indicates the amino-modified 5'end followed
      by a chain with 12 carbon atoms as spacer element at the 5'end

<400> SEQUENCE: 5

-continued

```
naggaagcca agatctcaa                                                    19

<210> SEQ ID NO 6
<211> LENGTH: 19
<212> TYPE: DNA
<213> ORGANISM: Artificial
<220> FEATURE:
<223> OTHER INFORMATION: Non sense probe
<220> FEATURE:
<221> NAME/KEY: misc_feature
<222> LOCATION: (1)..(1)
<223> OTHER INFORMATION: n indicates the amino-modified 5'end followed
      by a chain with 12 carbon atoms as spacer element at the 5'end

<400> SEQUENCE: 6
ncgtggattt cttcagagg                                                    19
```